US006772443B2

(12) United States Patent
Soerens et al.

(10) Patent No.: US 6,772,443 B2
(45) Date of Patent: Aug. 10, 2004

(54) BREATHABLE ELASTOMERIC GLOVE

(75) Inventors: Dave A. Soerens, Neenah, WI (US); Thomas Gregory Triebes, Alpharetta, GA (US); Kermit R. Littleton, Ellijay, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/334,124

(22) Filed: Dec. 30, 2002

(65) Prior Publication Data

US 2004/0123374 A1 Jul. 1, 2004

(51) Int. Cl.⁷ ............................................... A41D 19/00
(52) U.S. Cl. ............................ 2/161.6; 2/168; 428/221
(58) Field of Search ........................ 2/161.7, 167, 168; 428/36.8, 423.1

(56) References Cited

U.S. PATENT DOCUMENTS

| | | |
|---|---|---|
| 3,485,787 A | 12/1969 | Haefele et al. |
| 3,813,695 A | 6/1974 | Podell, Jr. et al. |
| 3,830,767 A | 8/1974 | Condon |
| 4,006,116 A | 2/1977 | Dominguez |
| 4,039,629 A | 8/1977 | Himes et al. |
| 4,041,103 A | 8/1977 | Davison et al. |
| 4,386,179 A | 5/1983 | Sterling |
| 4,481,323 A | 11/1984 | Sterling |
| 4,499,154 A | 2/1985 | James et al. |
| 4,511,354 A | 4/1985 | Sterling |
| 4,548,844 A * | 10/1985 | Podell et al. ................... 2/168 |
| 4,613,640 A | 9/1986 | Deisler et al. |
| 4,777,073 A | 10/1988 | Sheth |
| 5,112,900 A | 5/1992 | Buddenhagen et al. |
| 5,407,715 A | 4/1995 | Buddenhagen et al. |
| 5,534,350 A * | 7/1996 | Liou ........................ 428/423.1 |
| 5,670,263 A * | 9/1997 | Gazeley ...................... 428/492 |
| 5,695,868 A | 12/1997 | McCormack |
| 5,792,531 A * | 8/1998 | Littleton et al. ........... 428/36.8 |
| 5,855,999 A | 1/1999 | McCormack |
| 5,884,639 A | 3/1999 | Chen |
| 5,900,452 A | 5/1999 | Plamthottam |
| 5,993,972 A * | 11/1999 | Reich et al. .............. 428/423.1 |
| 6,015,764 A | 1/2000 | McCormack et al. |
| 6,075,179 A | 6/2000 | McCormack et al. |
| 6,172,177 B1 | 1/2001 | Wang et al. |
| 6,261,674 B1 | 7/2001 | Branham et al. |
| 6,288,159 B1 | 9/2001 | Plamthottam |
| 6,306,514 B1 | 10/2001 | Weikel et al. |
| 6,348,258 B1 | 2/2002 | Topolkaraev et al. |

FOREIGN PATENT DOCUMENTS

| | | |
|---|---|---|
| EP | 0815880 A3 | 1/1998 |
| EP | 0815880 A2 | 1/1998 |
| EP | 0931633 A2 | 7/1999 |
| EP | 1264684 A1 | 12/2002 |

OTHER PUBLICATIONS

PCT Search Report, Jan. 29, 2004.

* cited by examiner

Primary Examiner—Katherine Moran
(74) Attorney, Agent, or Firm—Dority & Manning, P.A.

(57) ABSTRACT

The present invention is directed to breathable elastomeric gloves. The gloves of the present invention may allow the transmission of water vapor while still providing an effective barrier to virus, bacteria, contaminants, bodily fluids, and the like. In general, a breathability additive may be incorporated into the polymer matrix of the or more layers of the glove to improve the breathability of the layer. For example, polyethylene oxide may be incorporated into a layer as a breathability additive.

25 Claims, 2 Drawing Sheets

BREATHABLE ELASTOMERIC GLOVE

BACKGROUND OF THE INVENTION

Gloves formed of elastomeric materials have been used in many applications: surgical gloves, examining gloves, food service gloves, and the like. Elastomeric materials have been found particularly suitable for such applications due to their physical characteristics. For example, elastomeric materials, in addition to having good elastic properties, exhibit good strength characteristics and may be produced so as to be impermeable not only to aqueous solutions, but also to many solvents and oils. Use of elastomeric gloves has provided an effective barrier between the wearer's hand and the environment, successfully protecting both from cross-contamination.

Elastomeric gloves are typically formed so as to be stretched somewhat during normal use. For example, some gloves, especially examination and surgical gloves, are formed so as to be stretched during donning, in order to fit tightly against the hand and provide good gripping and tactile characteristics during use. In addition, the gloves should be impermeable to undesired substances, in order to provide a barrier between the wearer and the environment in which the gloves are used. Unfortunately, these desired characteristics of elastomeric gloves may create a harsh environment for the wearer's skin. For example, perspiration is a common problem for glove wearers, and wearing gloves over a long period of time may be uncomfortable due to the trapped perspiration in the glove. In addition, the moist environment in the glove due to perspiration may exacerbate skin problems, including, for example, growth of fungi and yeast as well as bacterial and viral infections of the skin.

In the past, the skin contacting surface of the elastomeric articles were treated with a powder, such as talc or calcium carbonate powder to improve donning. The presence of the powders could also absorb some of the moisture and alleviate some of the problems the glove wearers faced. The use of powder was only partly successful, however, as there was a limited amount of moisture the powder could absorb. Additionally, in certain applications, such as clean-room type applications, powders could not be utilized at all.

What is needed in the art is an elastomeric glove which may provide the desired characteristics of either a powdered or a powder-free glove, while limiting or preventing the build-up of moisture between the hand and the glove during use. In other words, what is needed in the art is a breathable elastomeric glove.

Test Methods
Moisture Vapor Transmission Rate Test The following procedure is described for testing of the moisture vapor transmission rate (MVTR) for the breathable gloves of the invention. The MVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGUARD.RTM. 2500 (Hoechst Celanese Corporation). CELGUARD.RTM. 2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm.sup.2). The cups are then weighed, placed on a tray, and set in a forced air oven set at 100° F. (38° C.).

The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary test MVTR value is calculated as follows:

Test $MVTR=[(\text{grams weight loss over 24 hours})\times 7571]\div 24$

The relative humidity within the oven is not specifically controlled. Under predetermined set conditions of 100° F. and ambient relative humidity, the MVTR for CELGUARD.RTM. 2500 has been determined to be 5000 $g/m^2/$ 24 hours. Accordingly, CELGUARD.RTM. 2500 is run as a control sample with each test and the resulting values are corrected in accord with the variation of the control relative to its known MVTR.

Mocon Water Vapor Transmission Rate Test

A suitable technique for determining the WVTR (water vapor transmission rate) value of a material is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W model 100K manufactured by Mocon/Modern Controls, Inc. Minneapolis, Minn. A first test is made of the WVTR of the guard film and air gap between an evaporator assembly that generates 100 percent relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material.

This information is then used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F\rho_{sat}(T)RH/A\rho_{sat}(T)(1-RH))$$

where:

F=The flow of water vapor in cc/min., $\rho_{sat}(T)$=The density of water in saturated air at temperature T, RH=The relative humidity at specified locations in the cell, A A=The cross sectional area of the cell, and, $\rho_{sat}(T)$=The saturation vapor pressure of water vapor at temperature T

SUMMARY OF THE INVENTION

The present invention is generally directed to an elastomeric glove. More specifically, the glove of the present invention includes a substrate body made from at least one layer of a material and a breathability additive which is incorporated into the layer of the substrate body.

The material of the layer may be any material as is generally known in the art. For example, the material may be a material including one or more elastomeric block copolymers, hydrogel polymers, or polyurethane compositions.

The breathability additive incorporated into the layer of the substrate body may be polyethylene oxide. In one embodiment, the polyethylene oxide may be incorporated into the layer in an amount of between about 1 and about 70 parts per hundred by weight of the material. In one embodiment, the polyethylene oxide may be incorporated into the layer in an amount of between about 1 and about 30 parts per hundred by weight of the material.

The present invention is also directed to a process for forming breathable gloves. In general, the process includes providing a solvent, adding polyethylene oxide to the solvent to form a solution, adding the desired elastic material to the solution, forming a layer of the solution comprising the elastic material and the polyethylene oxide on a glove-shaped former, and drying the layer to form a glove on the former.

BRIEF DESCRIPTION OF THE FIGURES

A full and enabling disclosure of the present invention, including the best mode thereof to one of ordinary skill in the art, is set forth more particularly in the remainder of the specification, including reference to the accompanying figures in which.

DETAILED DESCRIPTION OF THE INVENTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations.

In general, the present invention is directed to breathable elastomeric gloves. For example, the gloves of the present invention may allow the transmission of water vapor while still providing an effective barrier to liquid which may carry virus, bacteria, contaminants, bodily fluids, and the like. The gloves of the present invention may reduce the amount of moisture build-up between the glove and the hand when worn, even when the gloves are worn for extended periods of time, making the gloves more comfortable to wear. In order to improve the breathability characteristics of a glove, the present invention is generally directed to incorporation of polyethylene oxide into the polymer matrix of one or more layers of the glove. The polyethylene oxide may be incorporated into the primary layer of the glove, a secondary layer of the glove, or into a coating layer of the glove.

The gloves of the present invention may be breathable elastomeric gloves. The term 'breathable' as used herein, is defined to mean allowing any transmission of water vapor across the axial direction of the substrate body forming the glove. For example, the gloves of the present invention may have a water vapor transmission rate of at least about 50 gsm/24 hours, though in certain embodiments, they may have a water vapor transmission rate lower than this exemplary water vapor transmission rate. In one embodiment, the gloves may have a water vapor transmission rate of greater than about 100 gsm/24 hours. For example, the gloves may have a water vapor transmission rate of greater than about 500 gsm/24 hours. In another embodiment, the gloves may have a water vapor transmission rate of greater than about 1000 gsm/24 hours. For example, the gloves may have a water vapor transmission rate of between about 1500 and about 2000 gsm/24 hours. Exemplary testing procedures for determining the moisture vapor transmission rate and the water vapor transmission rate of a breathable elastomeric glove are further described herein.

Figure 1:
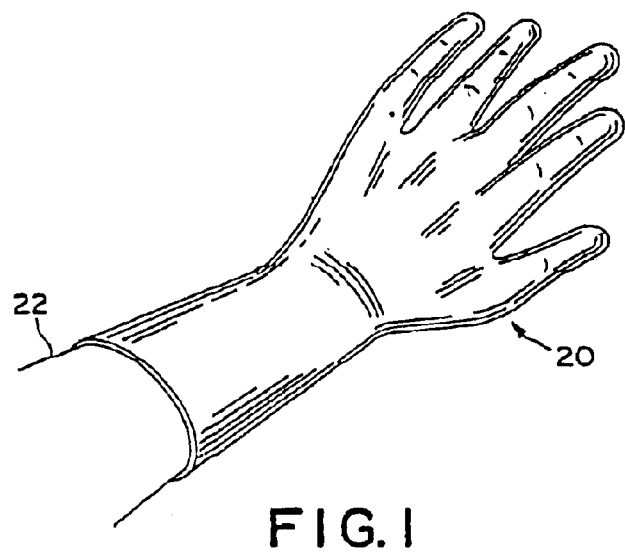
FIG. 1 is an embodiment of a glove according to the present invention.

Referring to FIG. 1, one embodiment of an elastomeric glove 20 is illustrated that may be placed on the hand of a user 22. The glove 20 includes a substrate body having the basic shape of the glove. The substrate body may generally be formed from any of a variety of polymeric elastomeric materials known in the art. In certain embodiments, the substrate body may include one or more layers of material. For instance, in some embodiments, the substrate body may include only a single breathable elastomeric layer according to the present invention. In other embodiments, however, the substrate body may include a primary elastomeric layer as well as additional layers. Additional layers may be, for example, secondary elastomeric layers in the glove interior, as well as donning layers and gripping layers.

In accordance with the present invention, one or more of the layers forming the substrate body of the glove may include a weight fraction of a polyethylene oxide polymer. The presence of the polyethylene oxide in the layer may not interfere with the properties of the layer and may improve water vapor transmission across the layer. In one embodiment, this layer may be combined with other breathable layers to form a multi-layer, breathable glove. The other layers of a multi-layer breathable glove may be formed according to the process of the present invention, or may be otherwise breathable. For example, other layers of a multi-layer breathable glove may be discontinuous across the glove surface, such that the layer is breathable, or may be otherwise breathable.

While not wishing to be bound by theory, it is believed that upon formation of the layer, the polyethylene oxide may be dispersed throughout the polymer/polyethylene oxide mixture, with 'islands', or areas of higher concentration of polyethylene oxide developing as the solvent is removed and the layer is formed. The concentration of polyethylene oxide 'islands' throughout the layer may be such that the islands may form in close proximity to one another, effectively forming a polyethylene oxide network throughout the layer which may permit molecular diffusion of water vapor across the layer, but block the passage of liquids. In essence, a tortuous path is created from one island to the other which permits the transfer of water vapor across the layer.

Any suitable polyethylene oxide or mixture of polyethylene oxides may be used in the gloves of the present invention. For example, polyethylene oxides may be used having the following general formula:

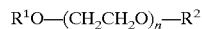

$$R^1O-(CH_2CH_2O)_n-R^2$$

wherein $R^1$ and $R^2$ are hydrogen or organofunctional groups. $R^1$ and $R^2$ may be the same or different.

In general, the molecular weight of the polyethylene oxide is not critical as long as enough polymer may be placed in the layer so as to produce the desired levels of breathability. For many applications, the molecular weight of the polyethylene oxide is greater than about 20,000, and particularly greater than about 50,000. In one embodiment, for instance, the polyethylene oxide may have a molecular weight of from about 100,000 to about 2 million.

High molecular weight polyethylene oxides are available from various commercial sources. Examples of polyethylene oxide resins that may be used in the present invention are commercially available from the Dow Chemical Corporation and are sold under the trade designations POLYOX N-205, POLYOX N-750, POLYOX WER N-10, and POLYOX WER N-80. The above four products are believed to have molecular weights of from about 100,000 to about 600,000 (g-mol). The polyethylene oxide resins may optionally contain various additives such as plasticizers, processing aids, rheology modifiers, antioxidants, UV light stabilizers, pigments, colorants, slip additives, antiblock agents, etc.

In order to incorporate the polyethylene oxide into the breathable layer, the polyethylene oxide resin(s) to be added to the elastomeric glove may be first dissolved in a solvent. A suitable solvent may be, for instance, one which may dissolve the polyethylene oxide as well as the polymeric material which may form the polymer matrix of the glove layer. A breathable layer of the glove may subsequently be formed from this single solution. For example, in one embodiment, the polymeric material which may form the matrix of the breathable layer may include an elastomeric material such as an elastomeric block copolymer. In this embodiment, any solvent capable of dissolving the block copolymer material may be used. For example, some suitable solvents that may be used include toluene and cyclohexane.

In another embodiment, the polymeric material forming the breathable layer may be a polyurethane composition such as may be used to form an elastomeric polyurethane layer of a glove. In this particular embodiment, the polyethylene oxide may be dissolved in an organic solvent suitable for polyurethane compositions such as toluene, xylene, tetrahydrofuran, dimethyl acetamide, methylene chloride, or a mixture thereof.

In one embodiment, the polyethylene oxide may be dissolved in a solvent which has been heated somewhat so as to promote dissolution of the polyethylene oxide. For example, the solvent may be heated to a temperature between about 30° C. and about 50° C. prior to addition of the polyethylene oxide. In one embodiment, the solvent may be heated to a temperature of about 40° C. prior to addition of the polyethylene oxide.

In another embodiment, the solvent is not heated prior to addition of the polyethylene oxide and the polyethylene oxide may be added to the solvent at ambient temperature (i.e., about 20° C.). For example, in certain embodiments, the solvent may be water, and the polyethylene oxide may be mixed into solution at ambient temperature.

The polyethylene oxide may generally be added to the solution prior to the other materials in an amount such that the resulting breathable layer may have the desired water vapor transmission characteristics and the polyethylene oxide may not interfere with the network of polymeric materials forming the matrix of the layer. For example, the polyethylene oxide may be added to the solution in an amount up to about 50% by weight, such as between about 1 and about 50 parts per hundred by weight of the material forming the matrix of the layer. In other embodiments, however, higher addition rates of polyethylene oxide are encompassed by the present invention. For example, in one embodiment, polyethylene oxide may be added to the solution in an amount up to about 70 parts per hundred weight of the material forming the matrix of the layer. In one embodiment, the polyethylene oxide may be added to the solution in an amount up to about 30 parts per hundred weight of the material forming the matrix of the layer. In another embodiment, the polyethylene oxide may be added to the solution in an amount up to about 10 parts per hundred weight of the material forming the matrix of the layer. In yet another embodiment, the polyethylene oxide may be added to the solution in an amount between about 4 and about 6 parts per hundred by weight of the material forming the matrix of the layer. For example, the solution may include polyethylene oxide in an amount of about 5 parts per hundred by weight of the material forming the matrix of the layer.

After dissolving the polyethylene oxide in a suitable solvent, the other polymeric materials which may form the breathable layer in conjunction with the polyethylene oxide may be added to the solution.

In one embodiment, elastomeric block copolymer materials may be used to form the matrix of the layer. For example, di-block copolymers having the general formula A-B, tri-block copolymers having the general formula A-B-A', or tetrablock copolymers having the general formula A-B-A'-B', where A and A' are the same or different, and B and B' are the same or different may be used. A and A' each being a thermoplastic polymer block, for example, A and A' may be a thermoplastic polymer block that contains a styrenic moiety, and B and B' being an elastomeric polymer block such as a conjugated diene or a lower alkene polymer. In general, the elastomeric block copolymers of the present invention may contain up to about 35% styrene by weight. For example, the block copolymers may contain from about 15% to about 30% styrene. In one embodiment, block copolymers such as those available from Kraton Polymers of Houston, Tex. may be used. In these block copolymers, the polystyrene is a thermoplastic with a glass transition temperature above room temperature ($T_g$ of about 200° F.) and the elastomeric block is a rubber with a glass transition temperature well below room temperature.

As such, the polystyrene and the elastomeric block are thermodynamically incompatible. Because of this incompatibility, the polystyrene blocks, being in minor proportion in the elastomeric polymer, may unite to form polystyrene domains that may be uniformly distributed throughout the elastomeric material. This creates a stable matrix similar to that of vulcanized polybutadiene, natural rubber, or styrene-butadiene rubber.

Some examples of suitable elastomeric materials include, but are not limited to, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, and combinations thereof. Moreover, combinations of polymers or copolymers may be in a single layer of an article or in separate layers, such as in a multi-layer article. In a multi-layer article, one or more of the layers may include polyethylene oxide according to the present invention.

Some block copolymers and methods for forming articles thereof are described in U.S. Pat. Nos. 5,112,900 to Buddenhagen, et al.; 5,407,715 to Buddenhagen, et al.; 5,900,452 to Plamthottam; and 6,288,159 to Plamthottam, which are incorporated herein in their entirety by reference thereto for all purposes.

In one embodiment of the present invention, mixtures of two or more S-EB-S copolymers may be utilized. In some instances, for example, two S-EB-S copolymers are utilized in which each block copolymer constitutes from about 40% to about 60% by weight of the mixture. In one embodiment, the first S-EB-S block copolymer has a solution viscosity of about 6500 cps at 25% by weight of copolymer in toluene (at 77° F.) and the second S-EB-S block copolymer has a solution viscosity of about 2000 cps at 10% by weight of copolymer in toluene (at 77° F.).

The use of S-EB-S block copolymer(s) in the substrate body may generally provide a number of benefits. For example, elastomers based upon the S-EB-S block elastomeric block copolymers are substantially resistant to attack by ozone or by other oxidative conditions. Moreover, the mechanical properties of the S-EB-S block copolymers may be selected to provide the desirable combination of tensile strength, elasticity, and tactility utilized in some applications.

Some commercially available examples of S-EB-S block copolymers, such as described above, include, but are not limited to, Kraton® G1650, Kraton® G1651, Kraton® G1652, which are available from Kraton Polymers of Houston, Tex. Kraton® G1650 is an S-EB-S block copolymer having a styrene/central block ratio of 28/72 and a Brookfield Viscosity in toluene solution (20% concentration by weight) at 77° F. of 1500 centipoise. Kraton® G1651 is an S-EB-S block copolymer having a styrene/central block ratio of 33/67 and a Brookfield Viscosity in toluene solution (20% concentration by weight) at 77° F. of 2000 centipoise. Kraton® G1652 is an S-EB-S block copolymer having a styrene/central block ratio of 29/71 and a Brookfield Viscosity in toluene solution (20% concentration by weight) at 77° F. of 550 centipoise.

Examples of suitable S-B-S tri-block copolymers available from Kraton Polymers of Houston, Tex. include those available under the trade designation KRATON D; for example, KRATON D 1101, KRATON D 1102 and KRATON D 1116. According to the Shell Chemical Company, KRATON D 1101 has a block styrene percent mass of 31%, a Shore A hardness of 69, and a solution viscosity of 4 Pa.s at 25% mass in toluene at 25° C. KRATON D 1102 has a block styrene percent mass of 28% and a Shore A hardness of 66. KRATON D 1116 has a block styrene percent mass of 23%, a Shore A hardness of 63, and a solution viscosity of 9 Pa.s at 25% mass in toluene at 25° C. These block copolymers are available as porous pellets and have a specific gravity of 0.94.

S-I-S tri-block copolymers which may be utilized in the present invention and are also available from Kraton Polymers under the trade designation KRATON D, include, for example, KRATON D 1107, KRATON D 1111, KRATON D 1112 and KRATON D 1117. KRATON D 1107 has a block styrene percent mass of 15%, a Shore A hardness of 32, and a solution viscosity of 1.6 Pa.s at 25% mass in toluene at 25° C. KRATON D 1111 has a block styrene percent mass of 22%, a Shore A hardness of 45, and a solution viscosity of 1.2 Pa·s at 25% mass in toluene at 25° C. KRATON D 1112 has a block styrene percent mass of 15%, a Shore A hardness of 25, and a solution viscosity of 0.9 Pa.s at 25% mass in toluene at 25° C. KRATON D 1117 has a block styrene percent mass of 17%, a Shore A hardness of 32, and a solution viscosity of 0.7 Pa·s at 25% mass in toluene at 25° C. The D 1111 grade is available as a porous pellet having a specific gravity of 0.93. The D 1107, D 1112 and D 1117 block copolymers are available as pellets having specific gravities of 0.92.

It should be understood that the breathable layers of the present invention are not limited to polymeric matrixes formed of the foregoing list of exemplary elastomeric block copolymers. Other suitable materials may alternatively be utilized in the disclosed breathable glove layers. For example, in one embodiment, a breathable elastomeric primary layer of a substrate body may be formed according to the processes of the present invention from a polyurethane rubber. In this embodiment, the polyethylene oxide may be dissolved in a suitable solvent for a polyurethane composition, as previously described, and the polyurethane composition may then be added to the solution. For example, in one embodiment, solution grade polyurethane compositions may be used including stoichiometric proportions of an aliphatic diisocyanate which may be reacted with a mixture of a higher molecular weight polyether diol and low molecular weight aliphatic diol in the presence of a small but effective amount of a condensation catalyst such as dibutyl tin dilaurate.

It should be further understood that the breathable glove layers of the present invention are not limited to the primary elastomeric layers of the glove. For instance, in one embodiment, a breathable layer of a glove may be formed according to the present invention which may be a breathable coating layer located on the primary layer of the substrate body. For example, after the formation of the primary layer of the glove, which may be a breathable layer according to the present invention or may alternatively be otherwise breathable, a breathable coating layer may be formed on a surface of the primary layer from a solution including the polymer which may form the matrix of the coating layer and polyethylene oxide in an amount up to about 70 parts per hundred by weight of the polymer forming the matrix of the layer. In one embodiment, the polyethylene oxide may be added in an amount of up to about 50 parts per hundred by weight. In another embodiment, the polyethylene oxide may be added in an amount of up to about 30 parts per hundred be weight. For instance, between about 1 and about 10 parts per hundred by weight of the material forming the matrix of the layer. For instance, a breathable donning layer may be formed on the inner surface of the glove. In one embodiment, the solution may contain the matrix-forming polymer and polyethylene oxide in an amount from about 4 to about 6 parts per hundred by weight of the matrix-forming polymer.

For instance, in one embodiment, subsequent to forming the primary layer of the glove from a solution including polyethylene oxide and one or more elastomeric block copolymers, a breathable donning layer may be formed on a surface of the primary layer by use of a toluene-based solution containing 1,2 syndiotactic polybutadiene and polyethylene oxide such that the donning layer is a breathable donning layer.

In a similar fashion, the glove may include a breathable gripping layer. For example, a breathable polymeric gripping layer may be formed from a solution of the polymer which may form the matrix of the gripping layer and polyethylene oxide in an amount such that the product gripping layer is a breathable layer.

In one embodiment, the breathable layer may be a breathable hydrophilic layer. For example, a breathable donning layer may be formed on an elastomeric glove from a solution including one or more hydrogel polymers, as are generally known in the art, and polyethylene oxide. In certain embodiments, hydrogel polymer layers may be somewhat breathable without the addition of any polyethylene oxide. In these particular embodiments, the process of the present invention may enhance the breathability of the layer.

Some hydrogel polymers and methods for forming hydrophilic layers thereof are described in U.S. Pat. Nos. 4,499,154 to James, et al.; 4,548,844 to Podell, et al.; and 3,813,695 to Podell, Jr., et al., which are incorporated herein in their entirety by reference thereto for all purposes. Exemplary hydrogel polymers include copolymers of hydroxyethylmethacrylate with methacrylic acid or with ethylhexyl acrylate or with both methacrylic acid and ethylhexyl acrylate.

Generally, a hydrogel polymer layer may be formed on a glove using an aqueous solution of the hydrogel polymer. In this embodiment, the polyethylene oxide may be simply added to the aqueous solution either before, after, or at the same time as addition of the hydrogel polymer to the water, and no extra solution-forming processes, such as heating of the solute, for example, need be carried out.

In one embodiment, a breathable hydrogel layer according to the present invention may include between about 4% and about 6% by weight polyethylene oxide and between about 94% and about 96% by weight of one or more hydrogel polymers as are generally known in the art. This hydrophilic layer may be deposited on the surface of a primary or secondary layer of the substrate body and may form a donning layer on the glove.

In addition, polyurethanes may also be utilized in a breathable donning layer according to the present invention. For example, in one embodiment, Hyslip 20022 (available from Noveon, Inc.) may be utilized in solution with polyethylene oxide to form a breathable donning layer according to the present invention. Hyslip 20022 contains 1-methyl-2-pyrrolidone and waterborne polyurethane.

The solution containing polyethylene oxide and the polymer materials may include other ingredients, as desired. For example, a polyethylene oxide/block copolymer solution may optionally have end-block compatible resins added to the polystyrene end-blocks. An added end-block compatible resin increases the glass transition temperature ($T_g$) of the block copolymer. The increased $T_g$ allows the final products to be used at higher temperatures. For instance, one suitable example of such an end-block compatible resin is poly (alpha-methyl styrene).

A plasticizer (e.g., an oil) may also be mixed with the polyethylene oxide/block copolymer solution to enhance the resulting properties of the elastomeric article. For example, in one embodiment, the plasticizer may include a mineral oil, such as a refined petroleum paraffinic hydrocarbon oil, which is described in Entries 6971 and 6972 of the Merck Index, Eighth Edition. The plasticizer may generally be added to the block copolymer/polyethylene oxide solution in any desired amount. For example, in some embodiments, the plasticizer comprises between about 30 to about 80 parts by weight of the total mass of the block copolymer(s).

All of the desired ingredients may be mixed in the solution with polyethylene oxide and the matrix-forming polymer of the layer for a sufficient time to reach a homogeneous solution and then filtered to remove any undesired particulate matter.

Figure 2:
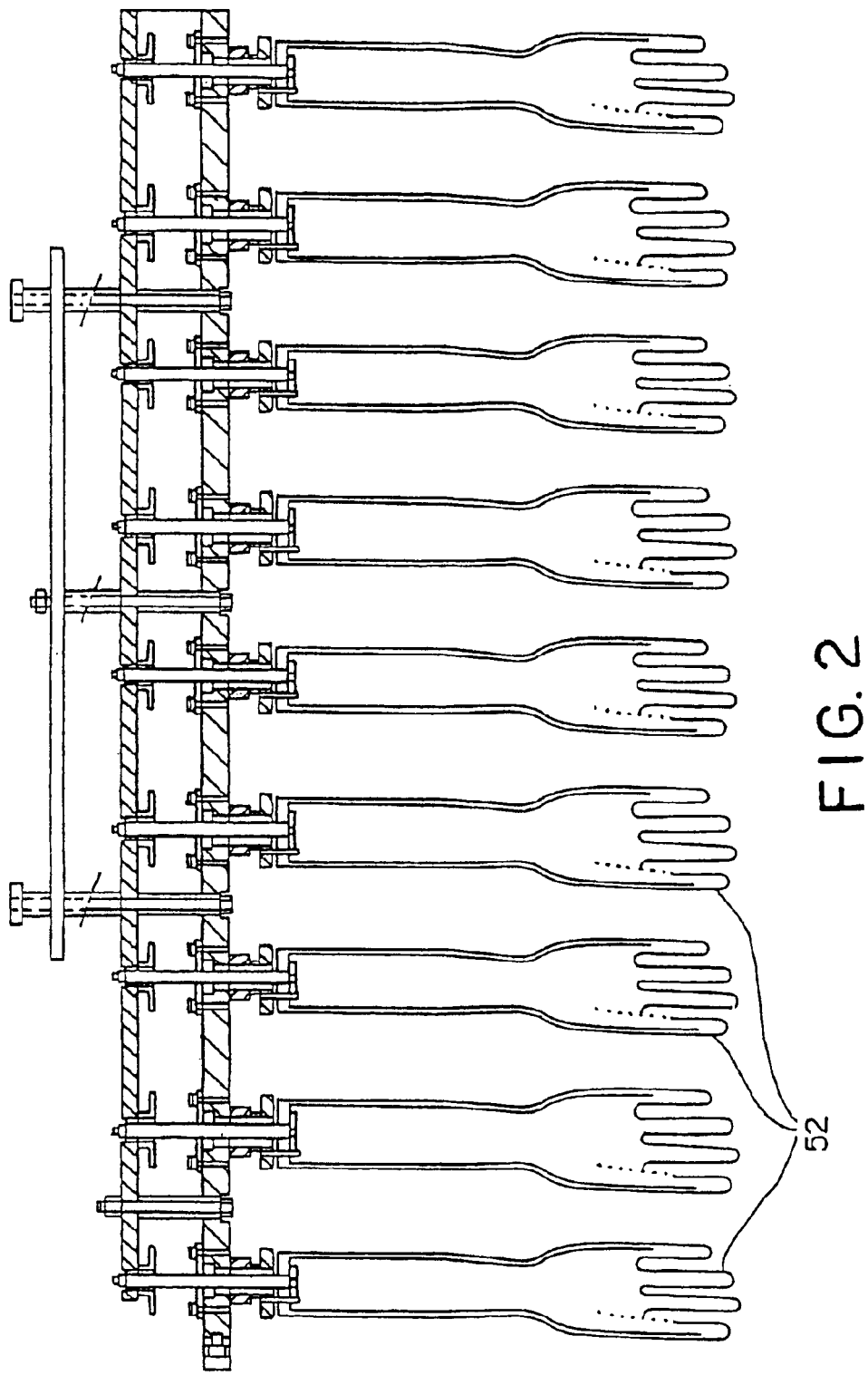
FIG. 2 is an illustration of glove-shaped formers that may be used in accordance with one embodiment of the present invention.

In general, the elastomeric gloves including one or more breathable layers of the present invention may be formed by any suitable process. For example, elastomeric glove formation techniques may utilize dipping, spraying, chlorination, drying, curing, as well as any other technique known in the art. In one embodiment, the breathable layer of the elastomeric glove may be formed by a series of dipping processes of a former of the shape of the finished article. FIG. 2 is an illustration of a series of glove molds or formers 52 which may be used to form the gloves of the present invention. The formers 52 shown in FIG. 2 are illustrated on a pallet as is conventionally used in a batch processing operation, but it should be understood that the process of the present invention may equally be utilized in a continuous or a semi-batch operation. A former 52 may generally be a contoured mold having a textured or smooth surface that may accept a series of coatings and release the formed article. Possible materials for the surface of former 52 may include any suitable surface material. For example, the surface of former 52 may be formed of ceramic, porcelain, glass, metal, or certain fluorocarbons.

The entire former is dipped into a dip tank containing polyethylene oxide, the matrix-forming polymer, and the solvent, such as xylene, water, etc. In one embodiment, for example, the former 52 is dipped into a dip tank that contains at least one styrene-ethylene-butylene-styrene (S-EB-S) block copolymer, polyethylene oxide, and a mutual solvent (e.g., toluene). A high shear mixer is utilized for a sufficient time to reach a homogeneous solution prior to dipping. After dipping, the former is removed slowly from the dip tank, leaving a thin, uniform layer of the liquid elastomer solution deposited onto the former. The former is dipped into the liquid solution a sufficient number of times to build up the desired thickness on the form. By way of example, the entire substrate body may have a thickness of from about 0.004 to about 0.012 inches. The glove is then allowed to dry and, in some embodiments, immediately stripped from the former. Methods for dip-forming S-EB-S layers are described in more detail in U.S. Pat. Nos. 5,112,900 to Buddenhagen, et al. and 5,407,715 to Buddenhagen, et al.

As previously mentioned, additional layers may be included in the glove, such as gripping or donning layers, for example. In some embodiments, these additional layers may be discontinuous across the surface of the glove such that the breathability of the glove will not be affected by the presence of the additional layer. In other embodiments, the additional layers may be continuous layers which may be breathable layers according to the present invention, i.e., through incorporation of a breathability additive, or may be otherwise breathable continuous layers. Discontinuous layers according to the present invention may be either macroscopically discontinuous, as when the material forming the layer is applied only to certain macroscopic areas of the glove, or may be microscopically discontinuous, as when the material forming the layer leaves microscopic fissures or holes in the layer upon drying of the layer.

Once the body of the glove is formed, such as described above, a bead roll station can, in some embodiments, be utilized to impart a cuff to the glove. For instance, the bead roll station may contain one or more bead rolls such that the former is indexed therethrough to be provided with cuffs. The formers may then be transferred to a stripping station. The stripping station may involve automatic or manual removal of the gloves from the formers. For example, in one embodiment, the gloves are manually removed from each former by turning each glove insideout as it is stripped from its corresponding former.

In some embodiments, after being stripped, the gloves may be subjected to a halogenation process, such as, for example, a chlorination process, to improve the surface characteristics of the glove, for example the donning slip characteristics. In one embodiment, the glove may be subjected to a chlorination process following stripping and tumble-drying (which may remove any residual moisture). For example, the glove may be chlorinated through immersion and optional agitation in an aqueous solution containing dissolved chlorine. In one embodiment, several gloves may be tumbled in a chlorine solution for a period of time between about 10 minutes and about 20 minutes.

After the optional halogenation process, the glove may be rinsed once more in water (preferable soft water) and dried. While chlorination of the gloves may decrease the breathability of the gloves somewhat in certain embodiments, the gloves of the present invention may still be breathable as defined in the present invention after a halogenation process.

If desired, a lubricant may also be applied to the donning surface of the glove. For example, a lubricant may be applied to the donning surface of the glove using a tumbling process. In one embodiment, a lubricant layer may overlay a donning layer to aid in donning the article when the user's body is either wet, damp, or dry. The lubricant layer, for example, may include a cationic (e.g., cetyl pyridinium chloride), an anionic (e.g., sodium lauryl sulfate), or a nonionic surfactant. For instance, in one embodiment, the lubricant layer contains a quaternary ammonium compound, such as Verisoft BTMS (available from Goldschmidt Chemical Corp. of Dublin, Ohio) and a silicone emulsion (AF-60) obtained from General Electric Silicone. Verisoft BTMS contains behnyl trimethyl sulfate and cetyl alcohol, while AF-60 contains polydimethylsiloxane, acetylaldehyde, and small percentages of emulsifiers. In another embodiment, the lubricant layer 32 contains a medical-grade silicone such as Dow Corning 365 silicone, which is believed to contain water, polydimethylsiloxane, octylphenoxy polyethoxy ethanol, propylene glycol, and polyethylene glycol sorbitan monolaurate.

Although various constructions and techniques for forming elastomeric gloves have been described above, it should be understood that the present invention is not limited to any particular construction or technique for forming the glove. For example, the layers described above may not be utilized in all instances. Additionally, other layers not specifically referred to above may be utilized in the present invention.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A glove comprising:
    a substrate body comprising at least one layer of a material, said substrate body having an inside surface and an outside surface; and
    a breathability additive incorporated into the at least one layer of the substrate body, the breathability additive comprising polyethylene oxide, the polyethylene oxide being present in the at least one layer in an amount between about 1 and about 70 parts per hundred by weight of the material.

2. The glove of claim 1, wherein the at least one layer is a primary elastomeric layer.

3. The glove of claim 2, wherein the primary elastomeric layer comprises an elastomeric block copolymer.

4. The glove of claim 3, wherein the elastomeric block copolymer is selected from the group consisting of styrene-ethylene-butylene styrene block copolymers, styrene-isoprene-styrene block copolymers, styrene-butadiene-styrene block copolymers, styrene-isoprene block copolymers, styrene-butadiene block copolymers, and mixtures thereof.

5. The glove of claim 2, wherein the primary elastomeric layer comprises a polyurethane rubber.

6. The glove of claim 1, wherein the at least one layer is a donning layer.

7. The glove of claim 6, wherein the donning layer comprises a hydrogel polymer.

8. The glove of claim 1, further comprising a lubricant located on the inside surface of the substrate body.

9. The glove of claim 8, wherein the lubricant comprises a silicone lubricant.

10. The glove of claim 1, wherein the at least one layer comprises polyethylene oxide in an amount between about 1 and about 50 parts per hundred by weight of the material.

11. The glove of claim 1, wherein the at least one layer comprises polyethylene oxide in an amount between about 1 and about 30 parts per hundred by weight of the material.

12. The glove of claim 1, wherein the at least one layer comprises polyethylene oxide in an amount between about 4 and about 6 parts per hundred by weight of the material.

13. The glove of claim 1, wherein the glove is a breathable glove.

14. A glove comprising:
    a substrate body made from at least one layer of a material selected from the group consisting of elastomeric block copolymers, hydrogel polymers, and polyurethanes, said substrate body having an inside surface and an outside surface; and
    a breathability additive incorporated into the at least one layer of the substrate body, the breathability additive comprising polyethylene oxide, the polyethylene oxide being incorporated into the at least one layer in an amount up to about 30 parts per hundred by weight of the material.

15. The glove of claim 14, wherein the elastomeric block copolymer is selected from the group consisting of styrene-ethylene-butylene-styrene block copolymers, styrene-isoprene-styrene block copolymers, styrene-butadienestyrene block copolymers, styrene-isoprene block copolymers, styrene-butadiene block copolymers, and mixtures thereof.

16. The glove of claim 14, further comprising a lubricant located on the inside surface of the substrate body.

17. The glove of claim 16, wherein the lubricant comprises a silicone lubricant.

18. The glove of claim 14, wherein the at least one layer comprises polyethylene oxide in an amount between about 1 and about 10 parts per hundred by weight of the material.

19. The glove of claim 14, wherein the at least one layer comprises polyethylene oxide in an amount between about 4 and about 6 parts per hundred by weight of the material.

20. The glove of claim 14, wherein the glove is a breathable glove.

21. A glove comprising:
a substrate body made from at least one layer of an elastic material comprising one or more block copolymers, said substrate body having an inside surface and an outside surface; and
a breathability additive incorporated into the at least one layer of the substrate body, the breathability additive comprising polyethylene oxide, the polyethylene oxide being incorporated into the at least one layer in an amount up to about 30 parts per hundred by weight of the elastic material.

22. The glove of claim 21, wherein the elastomeric block copolymer is selected from the group consisting of styrene-ethylene-butylene-styrene block copolymers, styrene-isoprene-styrene block copolymers, styrene-butadiene-styrene block copolymers, styrene-isoprene block copolymers, styrene-butadiene block copolymers, and mixtures thereof.

23. The glove of claim 21, further comprising a lubricant located on the inside surface of the substrate body.

24. The glove of claim 23, wherein the lubricant comprises a silicone lubricant.

25. The glove of claim 21, wherein the at least one layer comprises polyethylene oxide in an amount up to about 10 parts per hundred by weight of the elastic material.

* * * * *